(12) United States Patent
Pushpangadan et al.

(10) Patent No.: US 7,279,151 B2
(45) Date of Patent: Oct. 9, 2007

(54) HERBAL ORO-DENTAL CARE COMPOSITION AND PROCESS FOR PREPARING THE SAME

(75) Inventors: Palpu Pushpangadan, Uttar Pradesh (IN); Chandana Venkateswara Rao, Uttar Pradesh (IN); Sanjeev Kumar Ojha, Uttar Pradesh (IN); Kuttan Pillai Narayanan Nair, Uttar Pradesh (IN); Madan Mohan Pandey, Uttar Pradesh (IN); Ajay Kumar Singh Rawat, Uttar Pradesh (IN); Shanta Mehrotra, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 197 days.

(21) Appl. No.: 10/810,011

(22) Filed: Mar. 25, 2004

(65) Prior Publication Data

US 2005/0142074 A1    Jun. 30, 2005

Related U.S. Application Data

(63) Continuation of application No. PCT/IN03/00417, filed on Dec. 30, 2003.

(51) Int. Cl.
  *A61Q 11/00*  (2006.01)
  *A61K 6/00*  (2006.01)
  *A61K 36/00*  (2006.01)
  *A61K 36/752*  (2006.01)
  *A61K 36/58*  (2006.01)

(52) U.S. Cl. .................. 424/49; 424/48; 424/725; 424/736; 424/761; 424/750; 424/775; 424/58; 514/783; 514/900; 514/901; 514/902

(58) Field of Classification Search .............. None
See application file for complete search history.

(56) References Cited

U.S. PATENT DOCUMENTS

| 6,264,926 B1 * | 7/2001 | Farooqi et al. ............... 424/58 |
| 2002/0156130 A1 * | 10/2002 | Melman ................... 514/557 |
| 2003/0103914 A1 * | 6/2003 | Lawlor ..................... 424/58 |

FOREIGN PATENT DOCUMENTS

FR         2509609      * 1/1983

OTHER PUBLICATIONS http://pick4.pick.uga.edu/mp/20q?search=Citrus+aurantium&guide=Trees Morton, J. 1987. Sour Orange. p. 130-133. In: Fruits of warm climates. Julia F. Morton, Miami, FL. pp. 1-11.*

* cited by examiner

*Primary Examiner*—Frederick Krass
*Assistant Examiner*—Lezah Roberts
(74) *Attorney, Agent, or Firm*—Drinker Biddle & Reath LLP; Daniel A. Monaco

(57) ABSTRACT

This invention relates to novel dental compositions and methods for preventing dental plaque and caries formation and generally for inhibiting tooth decay and brightening/whitening teeth. The compositions of this invention comprise herbs such as *Citrus karna* raf., *Zanthoxylum armatum* D.C. and *Azadirachta indica* A. Juss. thereof which can be combined with pharmaceutically acceptable carriers or diluents to be administered in the form of conventional dental compositions. The compositions of the present invention, also preferably, contain *Mint*.

29 Claims, No Drawings

HERBAL ORO-DENTAL CARE COMPOSITION AND PROCESS FOR PREPARING THE SAME

FIELD OF INVENTION

The present invention relates to synergistic herbal oro-dental care composition used for preventing dental problems and a process for preparing the same. More particularly, the composition comprises herbs such as *Citrus karna, Zanthoxylum armatum, Azadirachta indica* and *Oriza sativa*.

BACKGROUND AND PRIOR ART

Bacterial aggregation on the teeth is known as plaque and causes dental caries, gingivitis, periodontitis and other gum diseases. A variety of microorganisms are present in the oral cavity. These range from the natural flora of the host to pathogenic species. Among these microorganisms are the gram-positive rods associated with the formation of plaque (a dense, enamel-adherent, microorganism-containing polysaccharide matrix). Specific areas, including periodontal and sub gingival spaces and interpapillary spaces of the tongue present environments that harbor bacteria. These spaces are difficult to reach by tooth brushing, and are only moderately affected by standard mouthwashes. Mechanical methods have been used for some time for the prevention of dental plaque but have not generally achieved sufficient results. Studies have shown that mechanical methods, such as the use of dental floss and inter-space brushes do not efficiently eliminate plaque. The persistence of these microorganisms in such environments greatly increases the risk of calculus and plaque build-up and carrier formation, which in turn presents the danger of gingival inflammation and periodontal disease. Thus, chemical plaque control as a substitute or supplement to mechanical methods is sought. *Azadiracta indica* is useful for anti bacterial/antiprotozoal activity and eliminating plaque from the tooth.

The essential oil obtained from the peal off of *Citrus karna* is useful for discoloration of teeth or tongue, desquamation and soreness of oral mucosa, while avoiding objectionable taste, toxicity and imbalance of the oral flora. Whereas chemicals like chlorhexidine are known to stain teeth, and has been know to cause tissue necrosis of the tongue and gums which may persist in tissue. The chemically also generally have poor cleansing qualities. Hydrogen peroxide has poor antibacterial properties, but works very well by using bursts of oxygen to flush out debris and cleanse the oral cavity.

The Botanical descriptions of various plants which are known for use in various dental problems include:

*Oriza sativa* Family: Poaceae

Botanical description: Rice is one of the oldest of food crops and has been in cultivation in India, China, Java and East Africa from very ancient time. Carbonized paddy grains and husks have been found in the excavations at Hastinapur (Uttar Pradesh) dated 1,000-800 B.C. It is an annual or perennial grass without a rhizome; leaves long and narrow, 30-50 cm.×1.2-2.5 cm., slightly pubescent with spiny hairs on the margin.

*Citrus karna* Raf. Family: Rutaceae

Botanical description: Medium trees 3-9 m tall, branches spreading spinous, spines long, sharp up to 5 cm long; Lvs. unifoliolate, petiole 1.0-1.5 cm long, marginate to very narrowly winged, lamina 9.0-10.5×5.5-6.0 cm, elliptic-ob-long or elliptic-ovate, base rounded, apex subacute/retuse, maggins serrulate, coriaceous, green, flowers axillary, solitary, or in 3 or 4 nate cymes, pedicels green, short ca 5 mm long, calyx copular 5 mm long, 7 mm broad, greenish-white with purplish tinged dorsally, 20 mm long 6 mm broad, base truncate, apex obtuse, imbricate in bulbs, wide opening, narrowly oblong, slightly asymmetric above; Flowers male and bisexual, stamens about 25, irregularly polyadlphous, filament short and long, white; anthers yellowish, disc greenish, annular, lobed, pistillodes minute, ovary green, 5 mm long, oblong; style greenish-white, 1 cm long; stigma capitate, 3-4 mm long; Disc green, annular; Fruits solitary or 3-4 in end of branchlets, fruiting pedicels short, attachment not strong, 9-12×8-10 cm base concave, apex sharply mammilate, mammae flat to broad, shape subglobose to subobovoid, epicarp orange-yellowish, thick, bumpy, warty, glandular (pitted) about 1 mm thick, glands dimorphic in cross section, mesocarp white, spongy, up to 2 cm thick, sweetish endocarp 8 or 9 segments, attachment strong, flesh orange-yellowish, juice sour, aromatic, central axis solid to semi hollow, white, juice glands slender, tapering; Seeds 10-12 mm long, 4-6 mm broad, ovoid—oblong, seed coat creamy white, streaked, inner coat grey-brownish, cotyledon white, chalazal spot reddish, polyembryonic.

*Azadirachta indica* A. Juss. Family: Meliaceae

Botanical description: Commonly called Neem, abundantly found in Indian sub-continent. It is a large sized evergreen tree, with alternate, exstipulate green coloured bitter leaves, new leaves may appear in March-April.

Phytochemistry: Siddiqui (1942) isolated crystalline bitter compound nimbidin, Butterworth and Morgan (1968) isolated azadiractin in crystalline form.

Medicinal use: *Azadirachta indica*, a plant used widely in Ayurveda, has been reported to have anti-inflammatory, immunomodulatory and adaptogenic properties. The present study evaluates its hepatoprotective role. Fresh juice of tender leaves of *Azadirachta indica* (200 mg/kg body wt. p.o.) inhibited paracetamol (2 g/kg body wt. p.o.)-induced lipid peroxidation and prevented depletion of sulfhydryl groups in liver cells. There was an increase in serum marker enzymes of hepatic damage (aspartate transaminase, alanine transaminase and alkaline phosphatase) after paracetamol administration. *Azadirachta indica* pretreatment stabilized the serum levels of these enzymes. Histopathological observations of liver tissues corroborated these findings (Yanpallewar, 2003). Neem is one of the most widely researched tropical tree, with almost all it's parts being put for a variety of uses. In the present study, the antibacterial effect of Neem mouthwash against salivary levels of streptococcus mutans and lactobacillus has been tested over a period of two months. Also it's effect in reversing incipient carious lesions was assessed. While streptococcus mutans were inhibited by Neem mouthwashes, with or without alcohol as well as chlorhexidine, lactobacillus growth was inhibited by chlorhexidine alone. The initial data appears to prove it's effect in inhibiting S. mutans and reversing incipient carious lesions, longer term clinical trials are essential (Vanka et. al. 2001)

Pharmacology: Hepatoprotective activity of *Azadirachta indica* leaf extract against paracetamol induced hepatic damage in rats has already been reported. In the present investigation effects of *Azadirachta indica* leaf extract on blood and liver glutathione, Na(+)K(+)-ATPase activity and thiobarbutiric acid reactive substances against paracetamol induced hepatic damage in rats have been studied with a view to elucidate possible mechanism behind its hepatoprotective action; it was interesting to observe that *Azadirachta indica* leaf extract has reversal effects on the levels of above mentioned parameters in paracetamol hepatotoxicity (Chattopadhyay 2003). Azadirone-1, a limonoidal constituent of *Azadirachta indica* is found to possess potent cytotoxic activity against a panel of human cancer cell lines in our in vitro studies. In vitro screening of a number of semi-synthetic analogues of 1 revealed that the alpha,beta-unsaturated enone moiety or its equivalent conjugated system in A-ring, C-7 acetyloxy/chloroacetyloxy or keto group in B-ring and the furan moiety are responsible for the activity of 1 and its analogues. Compound 1 and two of the semi-synthetic analogues 10 and 13 were found to possess good in vivo antitumor activity in modified hollow fiber animal models (Nanduri, 2003).

*Zanthoxylum armatum* D.C. Family: Rutaceae

Botanical description: Commonly known as Timur or Nepali Dhaniya, An armed, scandent or erect shrub or a small tree, 6 m. tall or more with dense foliage, found in a hot valleys of the Himalaya from Jammu to Bhutan at altitudes of 1,000-2,000 m. in Khasi hills at 600-1,800 m. and in the eastern ghats of in Orissa and Andhra Pradesh at 1,200 m. The dried pericarp of ripe fruit of *Zanthoxylum* spp. of family Rutaceae, has been used for epigastric pain accompanied by cold sensation, vomiting, diarrhea and abdominal pain due to intestinal parasitosis, ascariasis and used externally for eczema. The external features as characters of pericarp, the occurrence of hairs on fruit stalk, the presence and location of pigment and crystals of hesperidin, the thickness of the cell walls of endocarp and the presence and shape of nonglandular hairs on fruit stalk were important for the identification of these drugs.

Medicinal uses: The bark, fruits and seeds are extensively used in indigenous system of medicines as a carminative, stomachic and anthelmintic. An extract of fruits is reported to be effective in expelling round worms. Because of their deodorant, disinfectant and antiseptic properties, the fruits are used in dental troubles, and their lotion for scobies.

Phytochemistry: The essential oil obtained from seeds contains Linalool (64.1%), Linalyl acetate, citral, geraniol methyl cinnamate, limonene, sabinene etc. A new amide designated as armatamide (I)-along with two lignans, asarinin and fargesin, alpha- and beta-amyrins, lupeol, and beta-sitosterol-beta-D-glucoside-has been isolated from the bark of *Zanthoxylum armatum*. The structure of the new compound was deduced by spectral and chemical analysis as N-(4'-methoxyphenyl ethyl)-3, 4-methylenedioxy cinnamoyl amide (Kalia et al, 1999).

Pharmacology: A total of 11 methanol extracts obtained from four different Nepalese Zanthoxylum species were screened for their antiproliferative activity against the growth of human keratinocytes (HaCaT cells). The extract obtained from *Z. armatum* barks was highly active with an IC50 value of 11 micrograms/mL. Also, the extracts obtained from *Z. oxyphyllum* barks and roots with IC50 values of 53 and 57 micrograms/mL, respectively, showed potent activity. Their antiproliferative activity was not due to cytotoxic effects on cell membranes, as documented by the activity of lactate dehydrogenase released from the cytoplasm of keratinocytes, which did not exceed that of the control value. Rather, they also protected against radical-induced damage to model membranes stimulated with 2,2'-azo-bis(2-amidinopropane) dihydrochloride (Kumar & Muller, 1999).

OBJECTIVE OF INVENTION

The objective of the present invention is to provide a synergistic herbal oro-dental care composition useful for various dental problems.

Another objective of the present invention is to provide a composition for treating teeth, for the removal of plaque and caries, and for the prevention of the build-up of calculus.

Yet another objective of the present invention is to provide a novel composition useful in cleansing and brightening teeth and in the treating of plaque and gingivitis without any adverse side effects.

Another objective of the present invention is to provide dental compositions, which would cause little or no ecological imbalance of the oral flora.

Further objective of the present invention is to provide a composition comprising a combination of *Citrus karna, Zanthoxylum armatum* DC and *Azadirachta indica* and conventional toothpaste ingredients, wherein this composition possesses improved anti-plaque, anti-gingivitis, and cleansing activity.

Another objective of the present invention is to provide a method for treating teeth, which removes plaque and caries, without damaging the teeth.

Yet another objective of the present invention is to provide a method of treating teeth by dissolving away or dispersing plaque and caries, thus essentially eliminating the need for mechanical removal.

SUMMARY

The present invention provides a synergistic herbal oro-dental care composition comprising *Citrus karna, Zanthoxylum armatum, Azadirachta indica* and *Oriza sativa* and optionally one or more additives which not only provides beneficiary effects of the individual ingredients, but is also highly effective in various dental problems.

The present synergistic herbal oro-dental care composition comprising 20-30% by weight of powdered parts or extract of *Citrus karna,* 20-30% by weight of powdered parts or extract of *Zanthoxylum armatum,* 20-30% by weight of powdered parts or extract of *Azadirachta indica,* 20-30% by weight of powdered parts or extract of Oriza sativa and optionally one or more additives.

BRIEF DESCRIPTION OF TABLES

TABLE 1 Shows selection of volunteers of age as described below.

TABLE 2 Compares the taste of different compositions.

TABLE 3 Compares the odor of different compositions.

TABLE 4 Compares the texture of different compositions.

TABLE 5 Shows effect of the composition (F1) with and without citrus karna on dental problems and its effect TABLE 6 Shows effect of the composition (F4) on dental problems and its effect.

DETAILED DESCRIPTION OF INVENTION

Accordingly the present invention relates to a synergistic herbal Oro-dental care composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* and optionally one or more additives.

In an embodiment of the present invention, a synergistic herbal oro-dental care composition for the treatment of halitosis & mouth ulcers comprising the pastes or powders of charred husk of *Oriza sativa, Citrus karna, Azadirachta indica, Zanthoxylum armatum* and Mint 20-30%, 20-30%, 20-30%, 20-30%, and 0.5-5%, respectively.

In another embodiment of the present invention, the dental care composition is used in the form of powder, paste, gel, dental pack, dental floss, mouthwash and chewing gum.

In yet another embodiment of the present invention, the dental care composition is tooth powder.

In yet another embodiment of the present invention, wherein *Citrus karna* used is in powder form or as an extract and is obtained from citrus karna fruit peal or leaf or flowers.

In still another embodiment of the present invention, wherein the *Zanthoxylum armatum* is used in powder form or extract and is obtained from flowers, leaves roots or fruits of *Zanthoxylum armatum*.

In yet another embodiment of the present invention, wherein *Azadirachta indica* used is in powder form or as an alcoholic extract and is obtained from twigs, bark, seeds or leaves of *Azadirachta indica*.

In yet another embodiment of the present invention, wherein *Oriza sativa* used is in the form of carbon black charred husk.

In a further embodiment of the present invention, wherein the additives added are selected from the group consisting aromatizing agent, flavoring agent, sweeteners, colorants, polishing material, organic acid, alcohol, essential oils, exert carminative, antiseptic and analgesic agent.

In still further embodiment of the present invention, wherein alcohol used is ethanol.

In still another embodiment of the present invention, wherein aromatizing agent used is mint.

In yet embodiment of the present invention, wherein mint used are peppermint or pericarpmint.

In yet another embodiment of the present invention, wherein polishing material is abrasive particulate, having particle size up to 20 microns.

In yet another embodiment of the present invention, wherein organic acid used is acetic acid.

In yet another embodiment of the present invention, wherein flavoring agents used are natural or artificials cinnamon-clove beads.

In yet another embodiment of the present invention, wherein flavoring agents used are selected form cinnamon-clove beads, citrus flavor, such as orange and lemon and vanilla.

In still yet another embodiment of the present invention, wherein said composition is useful in treating discolored teeth, tongue, soreness of oral mucosa, stomatitis, ulcers, traumatic lesions of the mucus, chronic, recurrent cankers, plaque, halitos, gingivitics, dental extraction caries in teeth, gum, stomatitis, calculi, turtar formation, cankers, in protecting oral mucus against lipid peroxidation due to formation of free radicals and against contaminates (ozone, cigarette, smoke) and for soothing, curative, anti-inflammatory effect on epithelial lesions and reducing pain produced by putting false teeth in place.

Further embodiment of the present invention is a synergistic herbal oro-dental care composition, said process comprising the step of mixing 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* and optionally one or more additives.

In yet another embodiment of the present invention, powder form of the citrus karna, *Zanthoxylum armatum, Azadirachta indica* and *Oriza sativa* are obtained by drying leaves or rhizome or aerial parts of plants and grinding them in powder form Yet another embodiment of the present invention, *Citrus karna* used is in powder form and is obtained from *citrus karna* peal off.

Yet another embodiment of the present invention, wherein the *Zanthoxylum armatum* is used in powder form and is obtained from flowers, leaves, roots or fruits of *Zanthoxylum armatum*.

Yet another embodiment of the present invention, wherein *Azadirachta indica* used is in powder form and obtained from twigs, bark or leaves of *Azadirachta indica*. Yet another embodiment of the present invention, wherein *Oriza sativa* used is in the form of Carbon Black chared husk.

Still another embodiment of the present invention, wherein extracts of citrus karna, or *Zanthoxylum armatum* or *Azadirachta indica* or *Oriza sativa* are obtained by extracting powder parts of the same with the aqueous alcohol for 4 to 10 days under reduced pressure and at a temperature in the range of 40 to 60° C.

Yet another embodiment of the present invention, the ratio between the powdered plants and the aqueous alcohols is in the range of 1:8 to 1:15. Yet another embodiment of the present invention, wherein the additives added are selected from the group comprising aromatizing agent, flavoring agents, sweeteners, colorants, polishing material and organic acid.

Still another embodiment of the present invention, wherein aromatizing agent used is mint.

Yet another embodiment of the present invention, wherein mint used are peppermint or pericarpmint.

Yet another embodiment of the present invention, wherein polishing material is abrasive particulate, having particle size up to 20 microns.

Yet another embodiment of the present invention, wherein organic acid used is acetic acid.

Yet another embodiment of the present invention, wherein flavoring agents used are natural or artificial cinnamon-clove beads.

Yet another embodiment of the present invention, wherein flavoring agent used are selected form cinnamon-clove beads, citrus flavor such as orange and lemon and vanilla.

A further embodiment of the present invention relates to use of oro-dental care composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* and optionally one or more additives for treating discolored teeth, tongue, soreness of oral mucosa, stomatitis, ulcers, traumatic lesions of the mucus, chronic, recurrent cankers, plaque, halitosis, gingivitis, dental extraction caries in teeth, gum, stomatitis, calculi, tartar formation, cankers, in protecting oral mucus against lipid peroxidation due to formation of free radicals and against contaminates (ozone, cigarette, smoke) and for soothing, curative, anti-inflammatory effect on epithelial lesions and reducing pain produced by putting false teeth in place.

A further embodiment of the present invention relates to use of oro-dental care wherein, composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* and optionally one or more additives for treating discolored teeth, tonge, sorness of oral mucosa, stomatitis, ulcers, traumatic lesions of the mucus, chronic, recurrent cankers, plaque, halitos, gingivitics, dental extraction caries in teeth, gum, stomatitis, calculi, turtar formation, cankers, in protecting oral mucus against lipid peroxidation due to formation of free radicals and against contaminates (ozone, cigarette, smoke) and for soothing, curative, anti-inflammatory effect on epithelial lesions and reducing pain produced by putting false teeth in place.

In yet another embodiment of the present invention relates to use of oro-dental care wherein said composition is used in the form of paste, gel, mouthwash and chewing gum.

Yet another embodiment of the present invention relates to use of oro-dental care wherein said composition is used as tooth powder.

Yet another embodiment of the present invention relates to use of oro-dental care, wherein the *Citrus karna* is used in powder form or as an extract and as obtained from citrus karna fruit peal or leaf or flowers.

Yet another embodiment of the present invention relates to use of oro-dental care, wherein the *Zanthoxylum armatum* is used in powder form or as an extract and is obtained from flowers, leaves, roots or fruits of *Zanthoxylum armatum*.

Yet another embodiment of the present invention relates to use of oro-dental care, wherein *Azadirachta indica* used is in powder form or as an extract and as obtained from twigs, bark, seeds or leaves of *Azadirachta indica*.

Yet another embodiment of the present invention relates to use of oro-dental care, wherein *Oriza sativa* used is in the form of Carbon Black chared husk.

Still another embodiment of the present invention relates to use of oro-dental care, wherein the additives added are selected from the group consisting aromatizing agent, flavoring agent, sweeteners, colorants, polishing material, organic acid, alcohol, essential oils, exert carminative, antiseptic and analgesic agent.

Yet another embodiment of the present invention, relates to use of oro-dental care, wherein alcohol used is ethanol.

Yet another embodiment of the present invention relates to use of oro-dental care, wherein aromatizing agent used is mint.

Yet another embodiment of the present invention relates to use of oro-dental care, wherein mint used are peppermint or pericarpmint.

Yet another embodiment of the present invention relates to use of oro-dental care, wherein polishing material is abrasive particulate, having particle size up to 20 microns.

Yet another embodiment of the present invention relates to use of oro-dental care, wherein organic acid used is acetic acid.

Yet another embodiment of the present invention relates to use of oro-dental care, wherein flavoring agent used are natural or artificials cinnamon-clove beads.

Yet another embodiment of the present invention relates to use of oro-dental care, wherein flavoring agent used are selected from cinnamon-clove beads, citrus flavor such as orange, lemon and vanilla.

The dental product of the present invention is a tooth gel/dentifrice that cleans and brightens/whitens teeth. However, the instant dental product can also be a mouthwash, a paste, a gel, a dental pack, or dental floss. It may also be used to treat gum disease. It is equally well suited to prevent caries, calculi and tartar formation, as well as to help remove them. In order to maintain the preferred pH range in some occasions, it can be desirable to add a buffer system to the dental composition. The selection of the buffer is well known in the art and the buffer is preferably compatible with the other ingredients, that is, it should not have any negative effect on it, and should be non-toxic.

The present invention successfully cleans and brightens teeth while inhibiting and reducing the growth of plaque bacteria, which is achieved when acetic acid or other equivalent organic acid is utilized in combination with conventional dental ingredients in effective concentrations to treat the oral cavity. Small quantities of this unexpectedly simple and nevertheless active component are required to obtain effective inhibition of plaque and other bacteria. Since low quantities of active component can be used in the compositions of this invention, the side effects associated with use of the present invention is correspondingly reduced or eliminated. The compositions of this invention may be substantially solid or pasty in character such as dental cream, toothpaste, toothpowder or chewing gum. Such solid or pasty oral compositions may also contain polishing materials. Typical polishing materials are abrasive particulate materials having particle sizes of up to about 20 microns.

The compositions of the present invention may additionally contain sweeteners, flavorants and colorants. Suitable flavorings include both natural and artificial flavors, and mints such as peppermint, citrus flavors such as orange and lemon, artificial vanilla, cinnamon, various fruit flavors and the like. In one embodiment the flavoring agent comprises cinnamon-clove beads. The present invention also involves a method for treating teeth or gums to reduce plaque or gingivitis comprising applying to the surface of the teeth and/or gums the compositions of this invention as described above. The compositions can be applied to the teeth and gums by any conventional means such as brushing, spraying, painting or rinsing of the oral cavity and the like. The compositions not only cleans and brightens the teeth and retards plaque accumulation, but has been demonstrated to remove pre-existing plaque as well. Additionally, the compositions show a prolonged effect on plaque accumulation following cessation of treatment for at least about one week after use. The following examples are presented to further illustrate this invention. The examples are intended in an illustrative sense and not in a limitative sense. The present invention includes the embodiments described and shown and any equivalents thereof. All parts and percentages are on a weight basis unless otherwise indicated.

The dental product of the present invention is highly acceptable to consumers of all age group in respect of its taste, odor and texture. The present dental compositions are capable to prevent various dental problems. Although all the ingredients of the present invention are known to posses beneficial properties against dental problems, it should not be assumed that the product of the present invention is an obvious combination of the individual ingredients.

The use of any product does not only depend upon the bioactivity of the product, but also on the acceptance of the product. Products which do not have good flavor, odor, feel and other organoleptic properties have not been found as successful. Although each of the individual ingredient is known to posses beneficial bioactivity properties, their flavor, odor have not been found acceptable to people, for example *Azadirachta indica* has a very bitter taste due to which chewing. Its bark is very displeasing. Thus, in the present invention application the inventor has aimed for preparing a composition which, not only, provides the beneficiary effects of all ingredients, but is also capable to the users. The acceptance of the synergistic composition of the present invention has been tested using various age groups. Also, the synergistic composition of the present invention is hereafter referred to as F1. Four other compositions F2 to F5 have been prepared and compared with F1 to prove its synergistic effect.

In the following examples the process for preparing the synergistic compositions F2 to F5 are described.

The applicants have also conducted test on 100 volunteers to establish the synergistic nature of the composition F1.

EXAMPLE 1 # COMPOSITION (F1)

| | |
|---|---|
| 20% wt | Carbon black from Husk of *Oryza Sativa* |
| 30% wt | *Citrus karna* |
| 25% wt | *Azadirachta indica* |
| 20% wt | *Zathoxylum armatum* |
| Rest | Mint |

*Oriza Sativa, Citrus karna, Azadirachta indica*, and *Zathoxylum armatum* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form 0.15 g of starch is mixed with water and heated to form a paste.

The formulation is useful for the treatment of various dental problems.

EXAMPLE 2 # COMPOSITION (F2)

| | |
|---|---|
| 25% wt. | Carbon black from Husk of *Oryza Sativa* |
| 20% wt. | *Azadirachta indica* |
| 20% wt. | *Zathoxylum armatum* |
| Rest | Mint |

*Oriza Sativa, Azadirachta indica*, and *Zathoxylum armatum* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste.

The formulation is useful for the treatment of various dental problems.

EXAMPLE 3 # COMPOSITION (F3)

| | |
|---|---|
| 25% wt. | Carbon black from Husk of *Oryza Sativa* |
| 30% wt. | *Citrus karna* |
| 20% wt. | *Zathoxylum armatum* |
| Rest | Mint |

*Oriza Sativa, Citrus karna* and *Zathoxylum armatum* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste.

The formulation is useful for the treatment of various dental problems.

EXAMPLE 4 # COMPOSITION (F4)

| | |
|---|---|
| 20% wt | Carbon black from Husk of *Oryza Sativa* |
| 30% wt | *Citrus karna* |
| 25% wt | *Azadirachta indica* |
| Rest | Mint |

*Oriza Sativa, Citrus karna* and *Azadirachta indica* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form 0.15 g of starch is mixed with water and heated to form a paste.

The formulation is useful for the treatment of various dental problems.

EXAMPLE 5 # COMPOSITION (F5)

| | |
|---|---|
| 30% wt | *Citrus karna* |
| 25% wt | *Azadirachta indica* |
| 20% wt | *Zathoxylum armatum* |
| Rest | Mint |

*Citrus karna, Azadirachta indica*, and *Zathoxylum armatum* were collected and dried in shade. The dried material (1 Kg) is then powdered and extracted with 50% aqueous alcohol (3L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste.

EXAMPLE 6 # TESTING OF VARIOUS DENTAL COMPOSITIONS F1 TO F5.

The compositions are useful for the treatment of various dental problems. Samples of above composition(s) were given to volunteers on a prescribed performa during August 2002 to August 2003. Response was satisfactory. Sample size: 100 human beings/sample Area covered: India (State: Uttar Pradesh, City: Lucknow)—95% and outside the city Lucknow—5%

Methodology: Direct conversation with volunteers and questionnaire method.

TABLE 1

Selection of volunteers of age as described below.

| Years | F1 | | | F2 | | | F3 | | | F4 | | | F5 | | |
|---|---|---|---|---|---|---|---|---|---|---|---|---|---|---|---|
| Age | M | F | Total | M | F | Total | M | F | Total | M | F | Total | M | F | Total |
| <20 | 4 | 4 | 8 | 5 | 5 | 10 | 5 | 4 | 9 | 5 | 8 | 13 | 10 | 7 | 17 |
| 20–40 | 32 | 23 | 55 | 31 | 22 | 53 | 34 | 20 | 54 | 35 | 26 | 61 | 8 | 35 | 43 |
| >40 | 31 | 6 | 37 | 30 | 7 | 37 | 33 | 4 | 37 | 16 | 10 | 26 | 17 | 23 | 40 |
| Total | 67 | 33 | 100 | 66 | 34 | 100 | 72 | 28 | 100 | 56 | 44 | 100 | 35 | 65 | 100 |

The data represents the selection of male and female volunteers approached them selves or volunteers recommended or forwarded the formulation(s) to their colleagues.

TABLE 2

Compares the taste of different composition (s).

| | F1 | | F2 | | F3 | | F4 | | F5 | |
|---|---|---|---|---|---|---|---|---|---|---|
| Age Years | good/ accepted | Needs Improvement | good/ accepted | Needs Improvement | good/ accepted | Needs Improvement | good/ accepted | Needs Improvement | Good/ accepted | Needs Improvement |
| <20 | 06 | 02 | 04 | 06 | 04 | 05 | 06 | 07 | 12 | 05 |
| 20–40 | 51 | 04 | 28 | 25 | 20 | 34 | 30 | 31 | 05 | 38 |
| >40 | 35 | 02 | 25 | 12 | 30 | 07 | 06 | 20 | 20 | 20 |
| Total | 92 | 08 | 57 | 43 | 54 | 46 | 42 | 58 | 37 | 63 |

On the basis of the above result, it clearly shows that formulation F1 is highly acceptable compare to other formulations from the taste point of view and showed 92% good and accepted.

TABLE 3

Compares the odor of different composition (s).

| | F1 | | F2 | | F3 | | F4 | | F5 | |
|---|---|---|---|---|---|---|---|---|---|---|
| Age Years | good/ accepted | Needs Improvement | good/ accepted | Needs Improvement | good/ accepted | Needs Improvement | good/ accepted | Needs Improvement | good/ accepted | Needs Improvement |
| <20 | 05 | 03 | 03 | 07 | 03 | 06 | 10 | 03 | 11 | 06 |
| 20–40 | 54 | 01 | 33 | 20 | 24 | 30 | 40 | 21 | 07 | 36 |
| >40 | 30 | 07 | 29 | 08 | 25 | 12 | 18 | 08 | 25 | 15 |
| Total | 89 | 11 | 65 | 35 | 52 | 48 | 68 | 32 | 43 | 57 |

On the basis of the above result it clearly shows that formulation F1 (89%) is acceptable compare to other formulations from the odour point of view.

effective as compare to F1 formulation containing *Oriza Sativa, Citrus karna, Azadirachta indica* and *Zathoxylum armatum*. It was found that this composition F1 is highly

TABLE 4

Compares the texture of different composition (s).

| Age Years | F1 good/ accepted | F1 Needs Improvement | F2 good/ accepted | F2 Needs Improvement | F3 good/ accepted | F3 Needs Improvement | F4 good/ accepted | F4 Needs Improvement | F5 Good/ accepted | F5 Needs Improvement |
|---|---|---|---|---|---|---|---|---|---|---|
| <20 | 06 | 02 | 02 | 08 | 02 | 07 | 06 | 07 | 09 | 08 |
| 20–40 | 53 | 02 | 23 | 30 | 21 | 33 | 34 | 27 | 14 | 29 |
| >40 | 32 | 05 | 31 | 06 | 12 | 25 | 20 | 06 | 21 | 19 |
| Total | 91 | 09 | 56 | 44 | 35 | 65 | 60 | 40 | 44 | 56 |

On the basis of the above result it clearly shows that formulation F1 (91%) is acceptable compare to other formulations from the texture point of view.

acceptable to consumers and acceptable up to 92% people, 54% to 89% people found F1 composition is highly effective in bleeding gums, 48% to 76% people found the same

TABLE 5

Effect of the composition (F1) with and without *citrus karna* on dental Problems and its effect:

| S. No. | Problems* | Highly effective (%) With | Highly effective (%) Without | Moderately effective (%) With | Moderately effective (%) Without | Low/slow effective (%) With | Low/slow effective (%) Without | No action/(%) With | No action/(%) Without | Total Persons used (%) |
|---|---|---|---|---|---|---|---|---|---|---|
| 1. | Bleeding gums | 54 | 40 | 12 | 8 | 32 | 42 | 02 | 10 | 100 |
| 2. | Swollen gums | 48 | 42 | 26 | 23 | 23 | 30 | 3 | 5 | 100 |
| 3. | Toothache | 18 | 18 | 28 | 28 | 42 | 45 | 12 | 9 | 100 |
| 4. | Yellowing/staining of teeth | 35 | 30 | 26 | 22 | 29 | 40 | 10 | 8 | 100 |
| 5. | Loosening of teeth | 8 | 8 | — | — | 79 | 79 | 11 | 11 | 100 |
| 6. | Foul odour of mouth | 26 | 20 | 29 | 22 | 45 | 50 | — | 8 | 100 |
| 7. | Sensitivity to cold hot water/Food | 20 | 18 | 11 | 10 | 58 | 65 | 11 | 6 | 100 |

On the basis of the above result it clear that the formulation F1 is acceptable and highly effective and recommended, from this it is clear that the potency is increased.

composition is highly useful in swollen gums, 26 to 76% people found beneficial in odor of mouth, 8% to 35% people found it effective in loosening of teeth. On the basis of the

TABLE 6

Effect of the composition (F4) on Problems and its effect:

| S. No | Problems* | Highly effective (%) | Moderately effective (%) | Low/slow effective (%) | No action/(%) | Total Personsused (%) |
|---|---|---|---|---|---|---|
| 1. | Bleeding gums | 45 | 11 | 36 | 08 | 100 |
| 2. | Swollen gums | 38 | 30 | 29 | 03 | 100 |
| 3. | Toothache | 22 | 26 | 44 | 08 | 100 |
| 4. | Yellowing/staining of teeth | 31 | 30 | 19 | 20 | 100 |
| 5. | Loosening of teeth | 8 | 05 | 68 | 19 | 100 |
| 6. | Foul odour of mouth | 21 | 32 | 47 | — | 100 |
| 7. | Sensitivity to cold hot water/Food | 15 | 14 | 61 | 10 | 100 |

On the basis of the above results it clearly shows that formulation F4 can also be acceptable but it is not so above results indicates that the composition F1 is a acceptable, highly effective and recommended for use. The product is advised to be used with brush or finger either in the morning or night time or when discomfort is felt in the mouth and as used as mouth freshener.

The F2 composition contains powdered parts or extract of the three plant i.e *Oriza Sativa, Azadirachta indica* and *Zathoxylum armatum*. It was found that the acceptable level for this composition is only up to 57% people F3 composition contains powdered parts or extract of the four plant i.e *Oriza Sativa, Citrus karna* and *Zathoxylum armatum*. It was found that the acceptable level for the same is only up to 54% people F4 composition contains powdered parts or extract of three plants i.e., *Oriza Saliva, Citrus karna*, and *Azadirachta indica* which is acceptable but not so effective in comparison to formulation F1. Composition F5 contains powdered plants or extracts of three plants i.e. *Citrus karna, Azadirachta indica* and *Zathoxylum armatum*, which have very low acceptance level and effective to consumers.

The composition of the present invention can be delivered in common dental products, such as tooth pastes or dentifrices, tooth powders, mouthwashes, dental floss, toothpicks, chewing gum and the like. The dental product of the present invention cleans, and brightens and whitens teeth. It is also suitable for the treatment of gum disease. It is equally well suited for the prevention of caries, calculi and tartar formation as well as to help remove them. The composition of the present invention need not to be in semi-solid or solid form, i.e., paste or powder, but can be equally used as a solution to be brought adequately into contact with the teeth for a sufficient period of time to enable the plaque and caries to be dissolved and the teeth to be cleansed and brightened, e.g., as a conventional mouth rinse or mouth wash. The present invention also includes a method of treating teeth in dentistry, for the prevention of calculus, and/or the removal of caries, and/or the dissolving of plaque, and/or brightening/whitening teeth, comprising bringing into contact with the teeth a composition comprising acetic acid and preferably, a preparation containing conventional tooth paste or dentifrice ingredients. Conventional ingredients include, but are not limited to colorants, abrasives and polishing agents, flavoring agents, sweeteners, buffers, diluents, surfactants, gum, sodium fluoride, glycerol, chelating agents, and other ingredients well-known as dental additives and carriers. The preferred dental product of the present invention contains *Citrus karna* preferably, the composition also contains Neem. In accordance with the scope of this invention, it is desirable to add a buffer system to the dental composition. Such a buffer is preferably compatible with the preferred compounds, that is, it should not have any negative effect on same, and should be non-toxic i.e. 'Carbon black' obtained from the Charred husk of *Oriza sativa*.

ADVANTAGE OF PRESENT INVENTION

1. Since the components used in the formulation is of herbal origin the product is safe to be used orally, as they have no or nil adverse or side effects on the gums and teeth.

2. The product is economically viable and eco-friendly.

3. It doesn't contain tobacco or any other carcinogenic habit forming substance as ingredients to spoil the teeth and gums.

The invention claimed is:

1. A synergistic herbal oro-dental care composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* obtained from carbon black charred husk of *Oriza sativa*, and optionally one or more additives wherein said percentages are based on the weight of the composition.

2. A composition as claimed in claim 1, wherein said oro-dental care composition is in the form of a powder, paste, gel, dental pack, dental floss, mouthwash or chewing gum.

3. A composition as claimed in claim 2, wherein said oro-dental care composition is in the form of a tooth powder.

4. A composition as claimed in claim 1, wherein said powdered parts or extract of *Citrus karna* is obtained from *Citrus karna* fruit peal or leaf or flowers.

5. A composition as claimed in claim 1, wherein said powdered parts or extract of *Zanthoxylum armatum* is obtained from flowers, leaves, roots or fruits of *Zanthoxylum armatum*.

6. A composition as claimed in claim 1, wherein said powdered parts or extract of *Azadirachta indica* is obtained from twigs, bark, seeds or leaves of *Azadirachta indica*.

7. A composition as claimed in claim 1, wherein said additives are selected from the group consisting of aromatizing agents, flavoring agents, sweeteners, colorants, polishing material, organic acid, alcohol, essential oils, exert carminative, antiseptic and analgesic agent.

8. A composition as claimed in claim 7, wherein said alcohol is ethanol.

9. A composition as claimed in claim 7, wherein said aromatizing agent is mint.

10. A composition as claimed in claim 9, wherein said mint is peppermint or pericarpmint.

11. A composition as claimed in claim 7, wherein said polishing material is abrasive particulates having particle size up to 20 microns.

12. A composition as claimed in claim 7, wherein said organic acid is acetic acid.

13. A composition as claimed in claim 7, wherein said flavoring agents are natural or artificial cinnamon-clove beads.

14. A composition as claimed in claim 7, wherein said flavoring agents are at least one of orange, lemon and vanilla.

15. A method of oral care comprising,
providing a composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* obtained from carbon black charred husk of *Oriza sativa*, and optionally one or more additives wherein said percentages are based on the weight of the composition; and
applying said composition to a human oral cavity for treating at least one of discolored teeth, tongue, soreness of oral mucosa, stomatitis, ulcers, traumatic lesions of the mucus, chronic, recurrent cankers, plaque, halitosis, gingivitis, dental extraction, caries calculi, tartar formation, or cankers, or for protection of oral mucus against lipid peroxidation due to formation of free radicals.

16. The method of claim 15, wherein said composition is in the form of a powder, paste, gel, dental floss, mouthwash or chewing gum.

17. The method of claim 15, wherein said composition is in the form of a tooth powder.

18. The method of claim 15, wherein said powdered parts or extract of Citrus karna is obtained from *Citrus karna* fruit peal or leaf or flowers.

19. The method of claim 15, wherein said powdered parts or extract of *Zanthoxylum armatum* is obtained from flowers, leaves, roots or fruits of *Zanthoxylum armatum*.

20. The method of claim 15, wherein said powdered parts or extract of *Azadirachta indica* is obtained from twigs, bark, seeds or leaves of *Azadirachta indica*.

21. The method of claim 15, wherein said additives are at least one of aromatizing agents, flavoring agents, sweeteners, colorants, polishing material, organic acid, alcohol, essential oils, exert carminative, antiseptic and analgesic agent.

22. The method of claim 21, wherein said alcohol is ethanol.

23. The method of claim 21, wherein said aromatizing agent is mint.

24. The method of claim 23, wherein said mint is peppermint or pericarpmint.

25. The method of claim 21, wherein said polishing material is abrasive particulates having particle size up to 20 microns.

26. The method of claim 21, wherein said organic acid used is acetic acid.

27. The method of claim 21, wherein said flavoring agents are natural or artificial cinnamon-clove beads.

28. The method of claim 21, wherein said flavoring agents are at least one of orange, lemon and vanilla.

29. A method of oral care comprising, providing a composition comprising 20-30% by weight of powdered parts or extract of *Citrus karna*, 20-30% by weight of powdered parts or extract of *Zanthoxylum armatum*, 20-30% by weight of powdered parts or extract of *Azadirachta indica*, 20-30% by weight of powdered parts or extract of *Oriza sativa* obtained from carbon black charred husk of *Oriza sativa*, and optionally one or more additives wherein said percentages are based on the weight of the composition; and applying said composition to a human oral cavity for pain relief thereof.

* * * * *